US012747201B2

(12) United States Patent
Tang et al.

(10) Patent No.: US 12,747,201 B2
(45) Date of Patent: Sep. 29, 2026

(54) IODINATED COMPOUNDS HAVING RADIOCONTRAST PROPERTIES

(71) Applicant: Boston Scientific Scimed, Inc., Maple Grove, MN (US)

(72) Inventors: Yiqing Tang, Guildford (GB); Francesco Cuda, Basingstoke (GB); Cristian Parisi, Boston, MA (US); Koorosh Ashrafi, Purley (GB); Sean L. Willis, Farnham (GB); Curry Brown, Greenville, SC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 59 days.

(21) Appl. No.: 18/663,548

(22) Filed: May 14, 2024

(65) Prior Publication Data

US 2024/0360078 A1 Oct. 31, 2024

Related U.S. Application Data

(63) Continuation of application No. 17/572,905, filed on Jan. 11, 2022, now abandoned.

(60) Provisional application No. 63/136,332, filed on Jan. 12, 2021.

(51) Int. Cl.
*C07C 237/46* (2006.01)

(52) U.S. Cl.
CPC .................................. *C07C 237/46* (2013.01)

(58) Field of Classification Search
None
See application file for complete search history.

(56) References Cited

U.S. PATENT DOCUMENTS

| | | | |
|---|---|---|---|
| 4,250,113 | A | 2/1981 | Nordal et al. |
| 5,686,061 | A | 11/1997 | Li et al. |
| 5,709,846 | A | 1/1998 | Lem et al. |
| 7,205,385 | B2 | 4/2007 | Grimmond et al. |
| 10,206,946 | B2 | 2/2019 | Brandom et al. |
| 2005/0036946 | A1 | 2/2005 | Pathak et al. |
| 2007/0148096 | A1 | 6/2007 | Wistrand et al. |
| 2008/0064848 | A1 | 3/2008 | Atanasoska et al. |
| 2010/0209356 | A1 | 8/2010 | Wynn et al. |
| 2010/0221189 | A1 | 9/2010 | Newington et al. |

FOREIGN PATENT DOCUMENTS

| | | | |
|---|---|---|---|
| CN | 108191695 | A | 6/2018 |
| CN | 10819169 | B | 3/2019 |
| EP | 0108638 | B1 | 5/1984 |
| EP | 0498482 | A2 | 8/1992 |
| EP | 1798219 | A1 | 6/2007 |
| WO | 2003051451 | A1 | 6/2003 |
| WO | 2007094683 | A1 | 8/2007 |
| WO | 2009047316 | A1 | 4/2009 |
| WO | 2009047317 | A1 | 4/2009 |
| WO | 2009047319 | A1 | 4/2009 |
| WO | 2011110589 | A1 | 9/2011 |
| WO | 2015033092 | A1 | 3/2015 |
| WO | 2020003147 | A2 | 1/2020 |
| WO | 2020003153 | A1 | 1/2020 |
| WO | 2020198108 | A1 | 10/2020 |
| WO | 2022146749 | A1 | 7/2022 |

OTHER PUBLICATIONS

Bjorsvik et al. (Acta Chemica Scandinavica, 1995, 49, 115) (Year: 1995).*

Arokiaraj et al; "Magnetic Iodixanol- A Novel Contrast Agent and its Early Characterization," Journal of Medecine Vasculaire, 10 pages, 2018.

Ding et al; "Polymerization-Induced Self-Assembly of Large-Scale Iohexol Nanoparticles as Contrast Agents for X-Ray Computed Tomography Imaging," Polymer Chemistry, 10 pages, 2018.

International Search Report and Written Opinion for International Application No. PCT/US2022/011920 mailing date Apr. 14, 2022, 15 pages.

Priebe et al; "Synthesis and Characterization of Iodixanol," Acta Radiologica, 11 pages, 1995.

Yin et al; "Poly(iohexol) Nanoparticles as Contrast Agents for In Vivo X-Ray Computed Tomography Imaging," J Am Chem Soc., 9 pages, 2013.

Zhu et al; "Bioresponsive and Fluorescent Hyaluronic Acid-Iodixanol Nanogels for Targeted X-Ray Computed Tomography Imaging and Chemotherapy of Breast Tumors," Journal of Controlled Release, 11 pages, 2016.

* cited by examiner

*Primary Examiner* — Renee Claytor
*Assistant Examiner* — Jennifer C Sawyer
(74) *Attorney, Agent, or Firm* — Seager, Tufte & Wickhem, LLP

(57) ABSTRACT

The present disclosure pertains to iodinated compounds that comprise at least one 2,4,6-triiodobenzene moiety in which at least one of the hydrogens at 1-, 3- and 5-positions of the 2,4,6-triiodobenzene moiety is substituted by an iodinated substituent that comprises one or more iodophenyl-containing groups. The present disclosure also pertains to compositions containing such iodinated compounds and methods of making such iodinated compounds.

15 Claims, 5 Drawing Sheets

IODINATED COMPOUNDS HAVING RADIOCONTRAST PROPERTIES

PRIORITY

This application is a continuation application of U.S. application Ser. No. 17/572,905, titled "IODINATED COMPOUNDS HAVING RADIOCONTRAST PROPERTIES", filed on Jan. 11, 2022, which claims the benefit of U.S. Provisional Application Ser. No. 63/136,332, filed Jan. 12, 2021, the entireties of which are incorporated herein by reference.

FIELD

Among other aspects, the present disclosure relates to iodinated compounds having radiocontrast properties, to methods of making such iodinated compounds, and to medical supplies containing such iodinated compounds.

BACKGROUND

There is an ongoing need for new types of radiopaque enhancers that can be added to medical supplies, including medical devices and implants, that can replace the use of metallic materials as radiopaque enhancers. As a specific example, metal radiopaque additives such as tantalum used in liquid embolic formulations suffer from limitations of beam hardening which generates streak artefacts and strongly interfere with the resolution and structural details of neighbouring tissues or organs. Compounds that can be added to medical polymers to render them radiopaque under x-ray imaging would be highly desirable if such compounds (i) do not have a significant negative impact on the material properties of the polymers, (ii) do not cause undesirable imaging artefacts, (iii) can be dissolved in solvents or mixed into polymer melts for ease of processing, and/or (iv) do not leach out of the polymer or undergo significant degradation in use.

SUMMARY

The present disclosure relates to a family of organic iodinated compounds that contain a radiopaque moiety such as iodine as well as additional chemical groups that increase solubilisation, mixing and/or compatibilization with various materials with which the compounds are mixed. In various embodiments, the iodinated compounds contain hydroxyl groups that enhance interactions with hydrophilic groups in other materials with which they are mixed. This can aid the compatibility between the compounds and the materials and results in enhanced performance. These compounds have also the potential to be used instead of metals when some applications require the minimisation and/or elimination of electric and/or ferromagnetic conductivity.

In various aspects, the present disclosure pertains iodinated compounds that comprise at least one 2,4,6-triiodobenzene moiety in which at least one of the hydrogens at 1-, 3- and 5-positions of the 2,4,6-triiodobenzene moiety is substituted by an iodinated substituent that comprises one, two, three, four, or more iodophenyl-containing groups (in which the iodophenyl-containing groups contain only iodine atom substitutions on the phenyl group, and which may have one, two, three, four or five iodine atoms substituted for the hydrogen atoms of the phenyl).

In some embodiments, the iodophenyl-containing groups may be selected from one or more of mono-iodophenyl-containing groups, di-iodophenyl-containing groups, tri-iodophenyl-containing groups, tetra-iodophenyl-containing groups or penta-iodophenyl-containing groups.

In some embodiments, which can be used in conjunction with the above aspects and embodiments, the iodophenyl-containing groups may be selected from iodophenyloxy groups, iodophenylcarbonyloxy groups, or iodophenyl groups coupled via a cyclic acetal group or a carbamate group.

In some embodiments, which can be used in conjunction with the above aspects and embodiments, the iodinated substituent comprises a $C_2$-$C_6$-alkyl-amino group or a $C_2$-$C_6$-alkyl-carbonyl group in which $C_2$-$C_6$-alkyl hydrogens are substituted by (a) the one or more iodophenyl-containing groups and (b) zero, one or a plurality of hydroxyl groups. In more particular embodiments, the iodinated substituent comprises a $C_2$-$C_6$-alkyl-aminocarbonyl group or a $C_2$-$C_6$-alkyl-carbonylamino group in which $C_2$-$C_6$-alkyl hydrogens are substituted by (a) the one or more iodophenyl-containing groups and (b) zero, one or a plurality of hydroxyl groups. In certain embodiments, the $C_2$-$C_6$-alkyl is $C_3$-alkyl.

In some embodiments, the present disclosure pertains to an iodinated compound of the formula I:

I

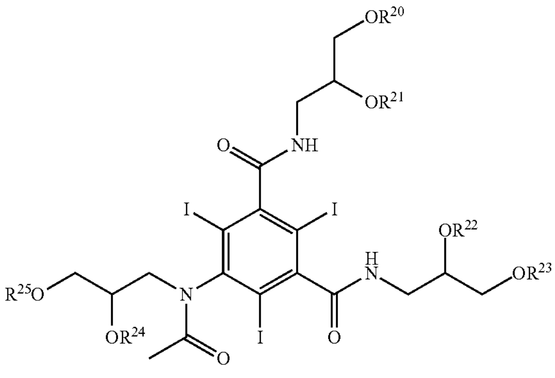

wherein each of $R^{20}$, $R^{21}$, $R^{22}$, $R^{23}$, $R^{24}$ and $R^{25}$ are independently selected from H and $R^{30}$, provided that at least one of $R^{20}$, $R^{21}$, $R^{22}$, $R^{23}$, $R^{24}$ and $R^{25}$ is $R^{30}$, where $R^{30}$ is selected from groups of the formula II, formula III, formula X:

II

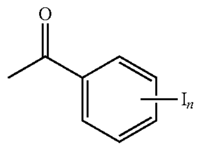

III

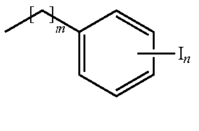

-continued

X

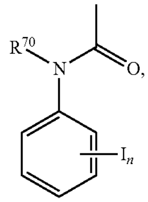

where m is 0, 1, 2, 3, 4, 5, 6, or more, where n is 1, 2, 3, 4 or 5, and where $R^{70}$ is H or $C_1$-$C_6$ alkyl (e.g., methyl, ethyl, n-propyl, isopropyl, butyl, hexyl), preferably H or $C_1$-$C_4$ alkyl; or wherein at least one of $R^{20}$+$R^{21}$, $R^{22}$+$R^{23}$ and $R^{24}$+$R^{25}$, taken together form a group of the formula IV:

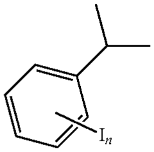

, where n is 1, 2, 3, 4, or 5; and any non-cyclized substituents $R^{20}$, $R^{21}$, $R^{22}$, $R^{23}$, $R^{24}$ and $R^{25}$ are H, in which case a

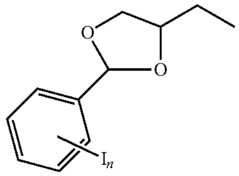

group is attached to at least one of the nitrogen atoms. Note that the formula I compound contains two $C_3$-alkyl-aminocarbonyl groups and one $C_3$-alkyl-amino group, which can collectively contain (a) one, two, three, four, five or six iodophenyl-containing —$OR^{30}$ groups and (b) zero, one, two, three, four or five hydroxyl groups.

In some embodiments, the present disclosure pertains to an iodinated compound of the formula V:

V

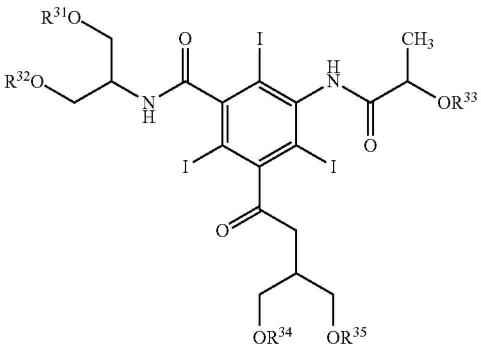

wherein each of $R^{31}$, $R^{32}$, $R^{33}$, $R^{34}$ and $R^{35}$ are independently selected from H and $R^{30}$, provided that at least one of $R^{31}$, $R^{32}$, $R^{33}$, $R^{34}$ and $R^{35}$ is $R^{30}$, wherein $R^{30}$ is defined above; or wherein at least one of $R^{31}$+$R^{32}$ and $R^{34}$+$R^{35}$, taken together form a group of the formula IV:

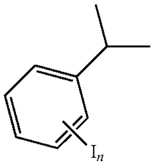

, where n is 1, 2, 3, 4, or 5 and any non-cyclized substituents $R^{31}$, $R^{32}$, $R^{33}$, $R^{34}$ and $R^{35}$ are H.

Note that the formula V compound contains two $C_3$-alkyl-aminocarbonyl groups and one $C_3$-alkyl-carbonylamino group, which can collectively contain (a) one, two, three, four or five iodophenyl-containing —$OR^{30}$ groups and (b) zero, one, two, three or four hydroxyl groups.

In some embodiments, the present disclosure pertains to an iodinated compound of the formula VI:

VI

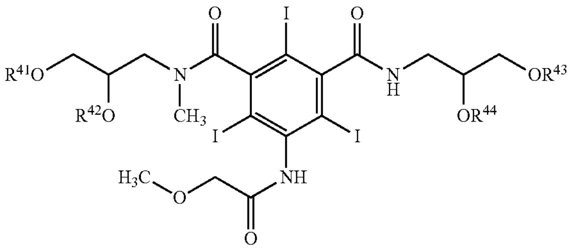

wherein each of $R^{41}$, $R^{42}$, $R^{43}$ and $R^{44}$ are independently selected from H and $R^{30}$, provided that at least one of $R^{41}$, $R^{42}$, $R^{43}$ and $R^{44}$ is $R^{30}$, where $R^{30}$ is defined above; or wherein or at least one of $R^{41}$+$R^{42}$ and $R^{43}$+$R^{44}$ taken together form a group of the formula IV:

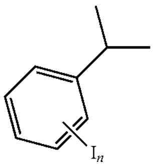

, where n is 1, 2, 3, 4, or 5 and any non-cyclized substituents $R^{41}$, $R^{42}$, $R^{43}$ and $R^{44}$ are H, in which case a

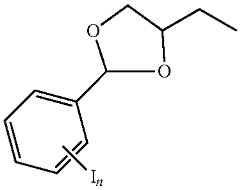

, group is attached to at least one of the nitrogen atoms.

In some embodiments, the present disclosure pertains to an iodinated compound of the formula VII:

VII

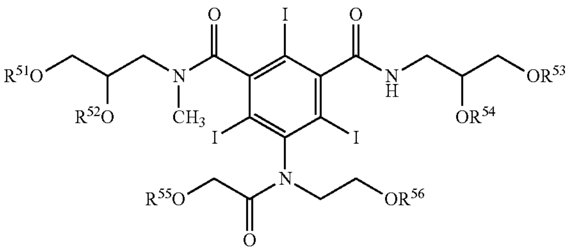

wherein each of $R^{51}$, $R^{52}$, $R^{53}$, $R^{54}$, $R^{55}$ and $R^{56}$ are independently selected from H and $R^{30}$, provided that at least one of $R^{41}$, $R^{42}$, $R^{43}$ and $R^{44}$ is $R^{30}$, where $R^{30}$ is defined above; or wherein at least one of $R^{51}+R^{52}$ and $R^{53}+R^{54}$ taken together form a group of the formula IV:

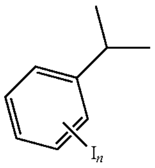

where n is 1, 2, 3, 4, or 5 and any non-cyclized substituents $R^{51}$, $R^{52}$, $R^{53}$, $R^{54}$, $R^{55}$ and $R^{56}$ are H, in which case a

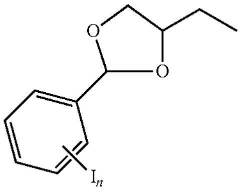

, group is attached to at least one of the nitrogen atoms.

In some embodiments, the present disclosure pertains to an iodinated compound of the formula VIII:

VIII

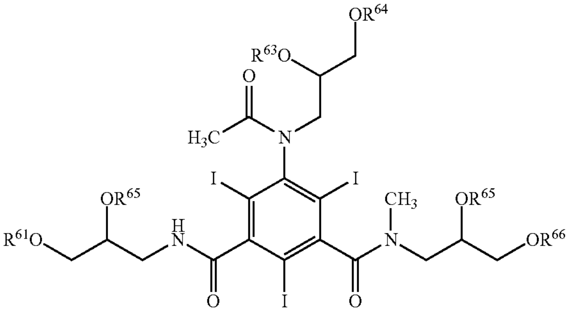

wherein each of $R^{61}$, $R^{62}$, $R^{63}$, $R^{64}$, $R^{65}$ and $R^{66}$ are independently selected from H and $R^{30}$, provided that at least one of $R^{61}$, $R^{62}$, $R^{63}$, $R^{64}$, $R^{65}$ and $R^{66}$ is $R^{30}$, where $R^{30}$ is defined above; or wherein at least one of $R^{61}+R^{62}$, $R^{63}+R^{64}$ and $R^{65}+R^{66}$ taken together form a group of the formula IV:

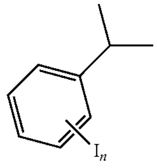

, where n is 1, 2, 3, 4, or 5 and any non-cyclized substituents $R^{61}$, $R^{62}$, $R^{63}$, $R^{64}$, $R^{65}$ and $R^{66}$ are H, in which case a

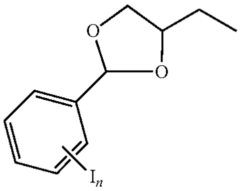

group is attached to at least one of the nitrogen atoms.

In some embodiments, the present disclosure pertains to an iodinated compound of the formula IX

IX

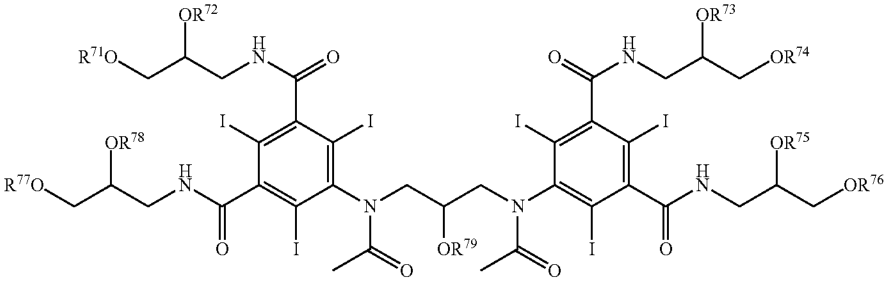

wherein each of $R^{71}$, $R^{72}$, $R^{73}$, $R^{74}$, $R^{75}$, $R^{76}$, $R^{77}$, $R^{78}$ and $R^{79}$ are independently selected from H and $R^{30}$, provided that at least one of $R^{71}$, $R^{72}$, $R^{73}$, $R^{74}$, $R^{75}$, $R^{76}$, $R^{77}$, $R^{78}$ and $R^{79}$ is $R^{30}$, wherein $R^{30}$ is defined above; or wherein at least one of $R^{71}$+$R^{72}$, $R^{73}$+$R^{74}$, $R^{75}$+$R^{76}$ and $R^{77}$+$R^{78}$ taken together form a group of the formula IV:

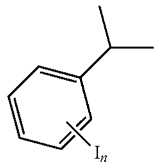

, where n is 1, 2, 3, 4, or 5 and any non-cyclized substituents $R^{71}$, $R^{72}$, $R^{73}$, $R^{74}$, $R^{75}$, $R^{76}$, $R^{77}$ and $R^{78}$ are H, in which case a

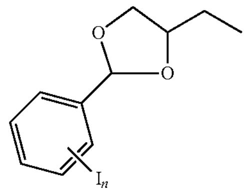

group is attached to at least one of the nitrogen atoms.

In any of the above structures, n may be 1, 2, 3, 4 or 5, but is typically 1, 2, 3 or 4, more typically, 3 or 4.

In any of the above structures, m may be 0, 1, 2, 3, 4, 5, 6 or more, more typically 0, 1 or 2.

In some embodiments, a molar ratio of hydroxyl groups to iodophenyl-containing groups in the iodinated compounds of the present disclosure may range from 0:1 to 10:1 or more, for example, ranging from 0:1 to 0.1:1 to 0.2:1 to 0.5:1 to 1:1 to 2:1 to 5:1 to 10:1 in some cases.

In further aspects, the present disclosure pertains to compositions that comprise one or more iodinated compounds, including one or more iodinated compounds in accordance with any of the above aspects and embodiments.

In various embodiments, such compositions comprise (a) one or more iodinated compounds in accordance with any of the above aspects and embodiments and (b) at least one polymer. Such compositions include liquid and solid compositions.

In certain embodiments, the at least one polymer is a hydrophilic polymer. In certain embodiments, the at least one polymer is a hydrophobic polymer.

Hydrophilic polymers for use in the compositions of the present disclosure include homopolymers and copolymers having repeating hydrophilic backbone units including ethylene oxide, propylene oxide, imide, amide, and ester units and homopolymers and copolymers having repeating units that comprise one or more pendant groups selected from the following: hydroxyl groups, carboxylic acid groups and salts thereof, carboxylic acid ester groups, amino groups, amide groups, sulfonic acid groups and salts thereof, phosphate groups and thiol groups.

Polymers for use in the compositions of present disclosure include polyvinyl alcohol homopolymers and copolymers, polyvinylpyrrolidone homopolymers and copolymers, poly (ethylene oxide) polymers and copolymers (e.g. poly(ethylene oxide)-poly(propylene oxide copolymers such as PEO-PPO-PEO block copolymers), polyoxazoline homopolymers and copolymers, polysulfonic acid homopolymers, copolymers and salts thereof, polyacrylic acid homopolymers, copolymers and salts thereof, poly(hydroxyalkyl acrylate) homopolymers and copolymers, polymethacrylic acid homopolymers, copolymers and salts thereof, poly(hydroxyalkylmethacrylate) homopolymers and copolymers, polyamide homopolymers and copolymers including polyamide block copolymers, polyacrylamide homopolymers and copolymers including poly(hydroxyalkylacrylamide) homopolymers and copolymers, poly methacrylamide homopolymers and copolymers including poly(hydroxyalkyl methacrylamide) homopolymers and copolymers, cellulose, methyl cellulose, carboxymethylcellulose, hydroxyethylcellulose, starch, chitosan, alginate, gelatin, polysaccharide gums, such as carageenan, guar gum, xanthan gum, gellan gum, locus bean gum and gum arabic, among others.

Polymers for use in the compositions of present disclosure also include polyolefin homopolymers and copolymers including homopolymers and copolymers of ethylene, propylene, butylene, butadiene, etc., polyvinyl chloride homopolymers and copolymers, polysiloxane homopolymers and copolymers, polysulfone homopolymers and copolymers, acrylate ester homopolymers and copolymers including homopolymers and copolymers of ethyl acrylate, propyl acrylate, butyl acrylate, etc, methacrylate ester homopolymers and copolymers including homopolymers and copolymers of methyl methacrylate, ethyl methacrylate, propyl methacrylate, butyl methacrylate, etc., polystyrene homopolymers and copolymers, fluorinated homopolymers and copolymers, polyacrylonitrile homopolymers and copolymers including poly(acrylonitrile-co-butadiene-co-styrene) (ABS), polyimide homopolymers and copolymers, polycarbonate homopolymers and copolymers, polyurethane homopolymers and copolymers, polyester homopolymers and copolymers including polyethylene terephthalate, polybutylene terephthalate and homopolymers and copolymers lactide, glycolide, and caprolactone, among others.

Compositions in accordance with the present disclosure may have radiopacity ranging, for example, from 10-10000 Hounsfield Units (HU) or more, for example, ranging from 10 HU to 25 HU to 50 HU to 100 HU to 250 HU to 500 HU to 1000 HU to 2500 HU to 5000 HU to 10000 HU.

Compositions in accordance with the present disclosure may have a range of iodine content. In some embodiments, compositions in accordance with the present disclosure may have an amount of iodine ranging from 1-80 wt %, typically 5-40 wt %, for example, 10-30 wt % or 15-25 wt %. In some embodiments, compositions in accordance with the present disclosure may have an amount of iodine ranging 2-1200 mg I/$cm^3$, typically 50-900 mg I/$cm^3$, for example, 100-800 mg I/$cm^3$, 150-500 mg I/$cm^3$ or 200-400 mg I/$cm^3$.

Other aspects of the present disclosure include medical supplies that comprise compositions in accordance with any of the above aspects and embodiments. Such medical supplies include medical devices and implants, for example, selected from catheters including catheter tubes, catheter balloons and catheter tips, guide wires, needles, endoscopes, filters, stents, stent grafts, vascular grafts, vascular access ports, embolization compositions, embolization particles, embolization devices, tissue bulking compositions, tissue bulking particles, tissue bulking devices, myocardial plugs, wound drains, gastroenteric tubes, urethral inserts, pacemaker leads, drug delivery depots, defibrillator leads, shunts, artificial hearts, heart valves, vascular valves, sutures, suture anchors, anastomosis clips and rings, tissue staples and ligating clips, cannulae, orthopedic prostheses, and joint prostheses.

In some embodiments, the composition comprises an entire medical supply (e.g., embolic or bulking particles or liquids, a drug delivery depot, a plug, a tube, a graft, a filter membrane, a valve, a suture etc.), a portion of a medical supply (e.g., a catheter balloon, catheter tube, catheter tip, marker band, etc.), a laminate layer or a coating on a medical supply (e.g., a laminate layer or a coating disposed over all or a portion of the medical supplies in the preceding paragraph).

In some embodiments the composition comprises PVA or co-polymers of PVA. In some embodiments the PVA or co-polymers thereof may comprise an iodinated aromatic group, covalently coupled to a backbone of the polyvinyl alcohol, in some embodiments the aromatic group is an iodinated phenyl group.

In some embodiments the composition comprises or is, a liquid embolic composition comprising PVA or co-polymers of PVA and one or more of the compositions described herein. The PVA or co-polymers of PVA may comprise covalently attached iodine, such as covalently attached iodinated phenyl groups. Typically, such compositions are provided as solutions in a solvent suitable for injection, such as DMSO. In such cases, the PVA or co-polymer of PVA precipitates form the solution in the blood to form an embolus. Examples of such PVA polymers and co-polymers are provided in WO2020/003147, WO2020/003153 and WO2011/110589.

In the case of a coating or laminate layer, the thickness of the composition may be varied to provide a desired radiopacity. As coating or laminate layers, compositions in accordance with the present disclosure may be applied to substrates that are polymeric, metallic, ceramic or a combination thereof. Coatings may be applied in any known manner, for instance from a solution, dispersion or melt that contains one or more polymers and one or more iodinated compounds, by spraying, brushing, pad printing, dipping, or the like, and also as powder coatings.

Other aspects of the present disclosure pertain to processes for making iodinated compounds including those described above. In some embodiments, such processes comprise reacting (a) at least one compound that comprises at least one 2,4,6-triiodobenzene moiety in which at least one of the hydrogens at 1-, 3- and 5-positions of the 2,4,6-triiodobenzene moiety is substituted by a polyhydroxylated substituent with (b) a compound of the formula XI, XII, or XIX:

XI

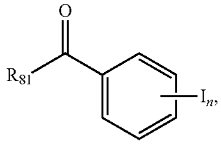

XII

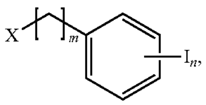

or

-continued

XIX

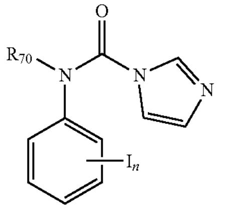

under conditions such that a linkage comprising a moiety selected from an ether, an ester, a cyclic acetal or a hemiacetal is formed, wherein n is 1, 2, 3, 4 or 5, wherein $R^{81}$ is selected from —H, —$CH_3$, —$CH_2CH_3$, —F, —Cl, —Br, —I, anhydride, —OH, an imidazolide, or an O-acylisourea, wherein $R^{70}$ is H or $C_1$-$C_6$ alkyl, wherein m is 0, 1, 2, 3, 4, 5, 6, or more, wherein X is —$O^-Na^+$ when m is 0, and wherein X is —F, —Cl, —Br or —I when m is 1, 2, 3, 4, 5, 6 or more. In the case of forming an ester linkage from compound XI, wherein $R^{81}$ is —OH, —$CH_3$ or —$CH_2CH_3$, acid catalysts could be used to enhance the esterification or transesterification; wherein $R^{81}$ is —F, —Cl, —Br, —I, or anhydride, the esterification could be catalysed by a tertiary amine or other bases. In the case of forming O-acylisourea, the catalyst N-ethyl-N'-(3-dimethylaminopropyl) carbodiimide hydrochloride (EDC) may be used to react with XI, wherein $R^{81}$ is —OH. In the case of forming an ether bond from XII where m is 0 and X is —$O^-Na^+$ (sodium phenolate), one or more the hydroxyl groups on the at least one compound from (a) (i.e., on the at least one compound that comprises at least one 2,4,6-triiodobenzene moiety in which at least one of the hydrogens at 1-, 3- and 5-positions of the 2,4,6-triiodobenzene moiety is substituted by a polyhydroxylated substituent) can be converted to one or more halide groups, such as using hydrogen halide, phosphorus halides, thionyl chloride, etc., to allow the reaction with the sodium phenolate moiety to form ether bonds through Williamson reaction. In the case where m is 1, 2, 3, 4, 5, 6 or more and X is halide, one or more hydroxyl groups on the at least one compound from (a) can be reacted with a compound of the formula XII under base conditions catalysed by NaOH, KOH, $Na_2CO_3$, $K_2CO_3$, NaH, etc., to form ether bonds through Williamson reaction. In the case of intermediate XIX an activated form of aniline or N-substituted aniline is formed by reaction with CDI, followed by reaction with at least one compound from (a). Alternatively the at least one compound from (a) may be activated by CDI followed by reaction with aniline or N-substituted aniline. The appropriate solvents for these reactions aforementioned may be selected, for example, from aprotic solvents, such as dimethyl sulfoxide, N-methylpyrrolidinone, N,N-dimethylformamide, N,N-dimethylacetamide, N-methyloxazolidinone, etc.

In some embodiments, the at least one compound that comprises at least one 2,4,6-trilodobenzene moiety in which at least one of the hydrogens at 1-, 3- and 5-positions of the 2,4,6-trilodobenzene moiety is substituted by a polyhydroxylated substituent may be selected from the following compounds:

XII

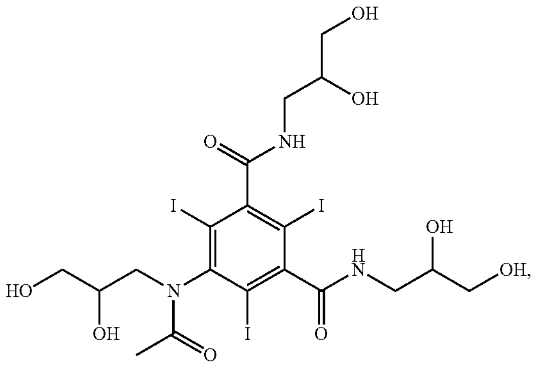

XIII

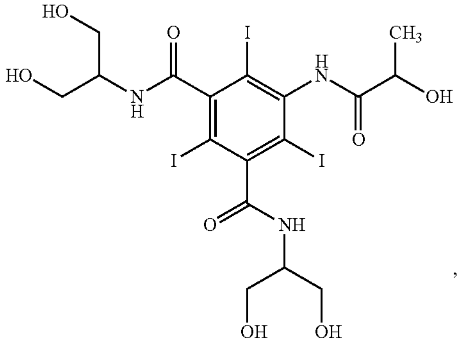

,

XIV

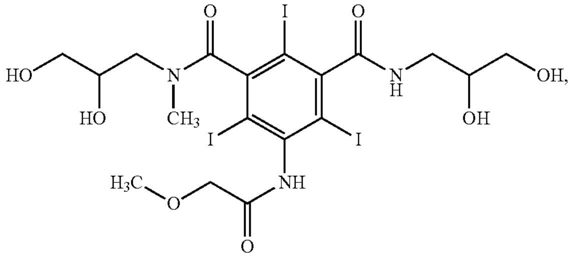

XV

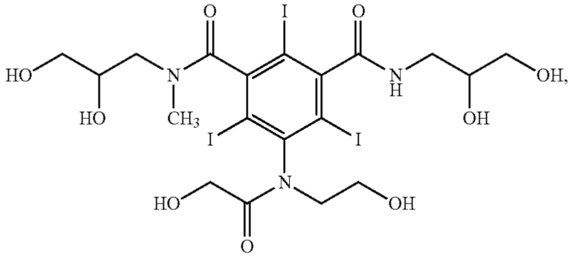

XVI

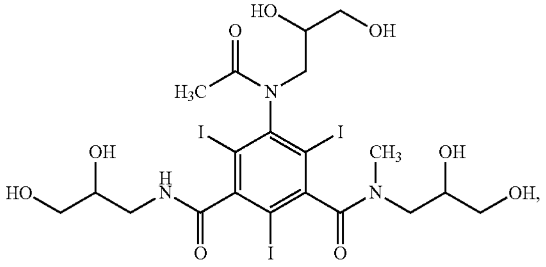

or

XVII

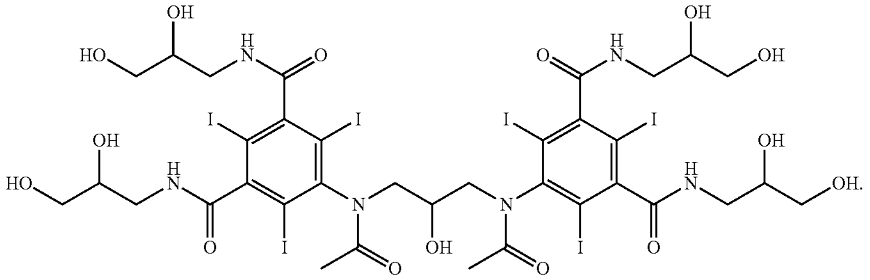

DETAILED DESCRIPTION OF PARTICULAR EMBODIMENTS

Figure 1A:
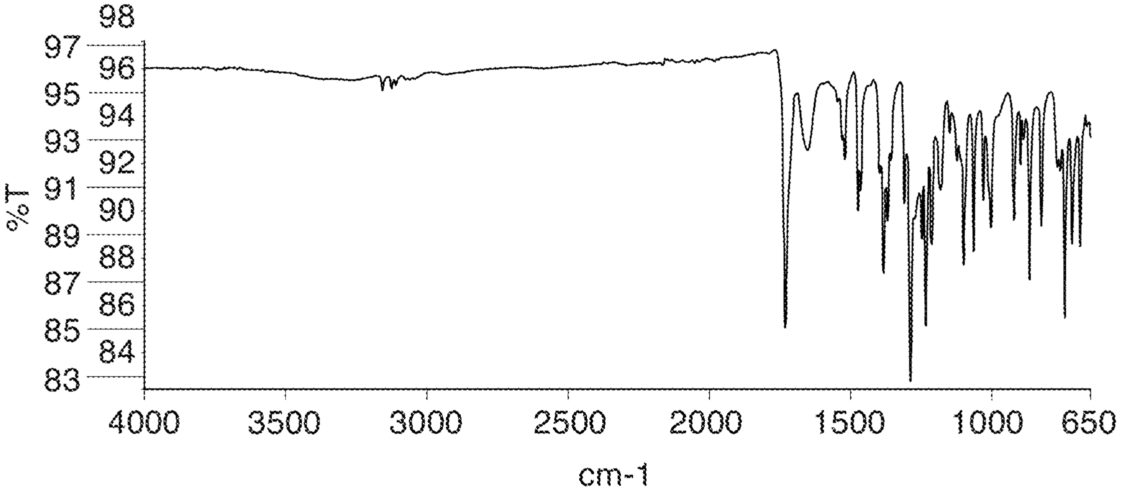
FIGS. 1A and 1B show the FTIR spectra of two iodinated compounds, in accordance with the present disclosure.

Iodinated compounds have been synthesized from hydrophilic contrast media, specifically, 5-(N-2,3-Dihydroxypropylacetamido)-2,4,6-triiodo-N,N'-bis(2,3-dihydroxypropyl) isophthalamide (iohexol) (Formula XII) and 5-[acetyl-[3-[acetyl-[3,5-bis(2,3-dihydroxypropylcarbamoyl)-2,4,6-triiodo-phenyl]amino]-2-hydroxy-propyl]amino]-N,N'-bis (2,3-dihydroxypropyl)-2,4,6-triiodo-benzene-1,3-dicarboxamide (iodixanol) (Formula XVII), by reaction of the available hydroxyl groups with further iodinated groups. The obtained compounds contain a high level of iodine, which may be further tuned by controlling the level of hydroxyl groups reacted. By changing the ratio of hydrophobic iodinated moieties to hydrophilic OH groups, the interaction between the additives and the media may be regulated to achieve desired viscosity fluid and solidification properties.

In addition to iodinated compounds synthesis, a liquid embolic formulation prepared from iodinated PVA with hydrophilic functional groups and an iodinated compound in accordance with the present disclosure is also described. Injectability and radiopacity were demonstrated. Embolization ability was also demonstrated by delivery of the liquid embolic material to a 5 mm silicone tube perfused a constant flow of phosphate buffered saline (PBS) at 400 ml/min of flow rate (at 37° C.).

Also described is a coating composition prepared from PVA and an iodinated compound in accordance with the present disclosure. The composition is used to coat a catheter balloon. The coating is cohesive, flexible and is stable upon repeated balloon inflation/deflation cycles and exhibits radiopacity as described more fully below. Radiopaque coatings are desirable for balloon catheter coatings since the location of the edges of the balloon and balloon surface can be tracked in real time within the body under fluoroscopy. In the current clinical practice, a balloon filled with a contrast medium to enable radiopacity; however, a radiopaque polymer coating on the outside of the balloon is an alternative to the need for contrast and allow for use of saline to inflate the balloon. Thus, by providing a radiopaque polymer coating on the outside of the balloon, balloon catheters can be improved. Because the radiopaque polymer coating can be dipped, sprayed and pad printed onto the balloon, it is possible to create different patterns of the radiopaque coating on the balloon. These patterns could also be designed in order to provide useful information to a medical profession during an interventional procedure.

Example 1: Preparation of Iohexol and Iodixanol Derivatives

Iohexol (see Formula XII) powder (2.5 grams) was charged into a 250 mL of flask and dissolved in 10 mL of anhydrous DMSO by heating to 50° C. under magnetic stirring. 2,3,5-triiodobenzoic acid (TIBA) (9.9 grams) was dissolved in 15 mL of anhydrous DMSO in a 100 mL round bottom flask, followed by adding carbonyl diimidazole (CDI) powder (3.21 grams) very slowly at room temperature with constant agitation to allow the release of generated carbon dioxide. The addition/agitation took about 30 min, and CDI-activated TIBA was generated. This reaction mixture was then added into the flask containing the Iohexol solution, and reaction was carried out under magnetic stirring at 60° C. for 20 hr. After reaction, the mixture was poured into 500 mL of sodium carbonate water solution (2.5 w/w %) with vigorous magnetic stirring. White precipitates were received and filtered through a Buchner funnel. The white powder was further washed with deionised water to remove residual $Na_2CO_3$ salt and solvent until neutral pH reached in the washing solution. The white powder was then extracted three times with 500 mL of acetonitrile at 60° C. under magnetic stirring. The final product was collected and dried in vacuum at 40° C. overnight, and 5.5 grams of powder was yielded.

Iodixanol (see Formula XVII) powder (3.0 gram) was charged into a 250 mL of flask and dissolved in 10 mL of anhydrous DMSO by heating to 50° C. under magnetic stirring. 2,3,5-triiodobenzoic acid (TIBA) (9.2 grams) was dissolved in 15 mL of anhydrous DMSO in a 100 mL round bottom flask, followed by adding carbonyl diimidazole (CDI) powder (2.98 grams) very slowly at room temperature with constant agitation to allow the release of generated carbon dioxide. The addition/agitation took about 30 min, and CDI activated TIBA was generated. This reaction mixture was then added into the flask of Iodixanol solution, and reaction was carried out under magnetic stirring at 60° C. for 20 hr. After reaction, the mixture was poured into 500 mL of sodium carbonate water solution (2.5 w/w %) with vigorous magnetic stirring. White precipitates were received and filtered through a Buchner funnel. The white powder was further washed with deionised water to remove residual $Na_2CO_3$ salt and solvent until neutral pH reached in the washing solution. The white powder was then extracted three times with 500 ml of acetonitrile at 60° C. under magnetic stirring. The final product was collected and dried in vacuum at 40° C. overnight, and 6.2 grams of powder was yielded.

Table 1 lists the theoretical iodine content and element analysis results of Iohexol and Iodixanol derivatives obtained using the reaction processes described above. The products were targeted to achieve either 100% reacted-OH groups (referred to as Iohexol derivative (I) and Iodixanol derivative (III)) or 50% reacted-OH groups (referred to as Iohexol derivative (II) and Iodixanol derivative (IV)) on these two compounds. Only about 65% to 68% iodine content were obtained, which could be explained as the effect of steric hinderance from activated intermediate 2,3,5-triiodobenzoic acid imidazolide.

TABLE 1

| Compound | Target molecular weight | Iodine content in theory (%) | Experimental iodine content (%) |
|---|---|---|---|
| Iohexol | 821.14 | 46.36 | — |
| Iohexol derivative (I) | 3711.18 | 71.80 | 68.70 |
| Iohexol derivative (II) | 2748.33 | 69.26 | 67.40 |
| Iodixanol | 1550.19 | 49.12 | — |
| Iodixanol derivative (III) | 5885.16 | 71.14 | 66.66 |
| Iodixanol derivative (IV) | 3958.29 | 67.31 | 65.65 |

Figure 1B:
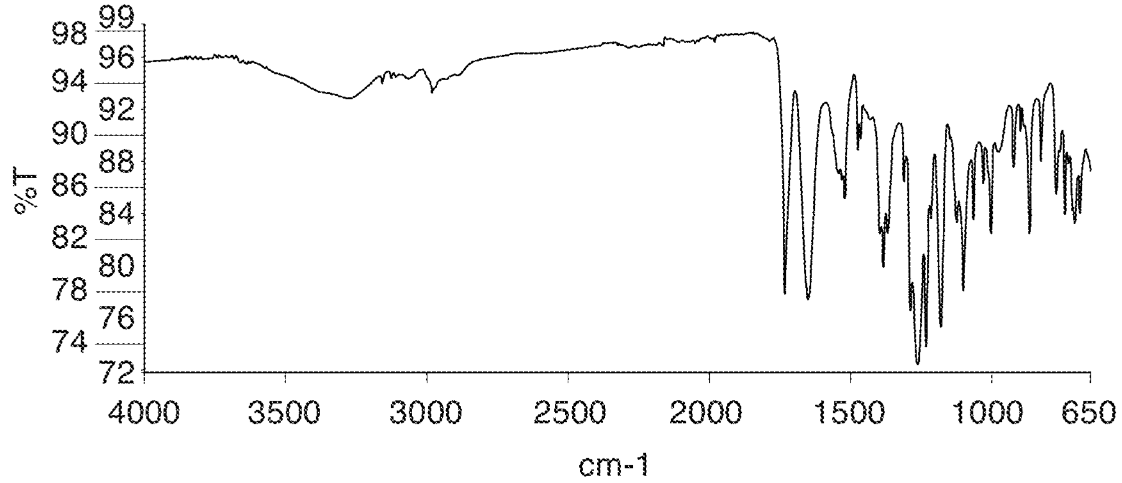
Figure 2A:
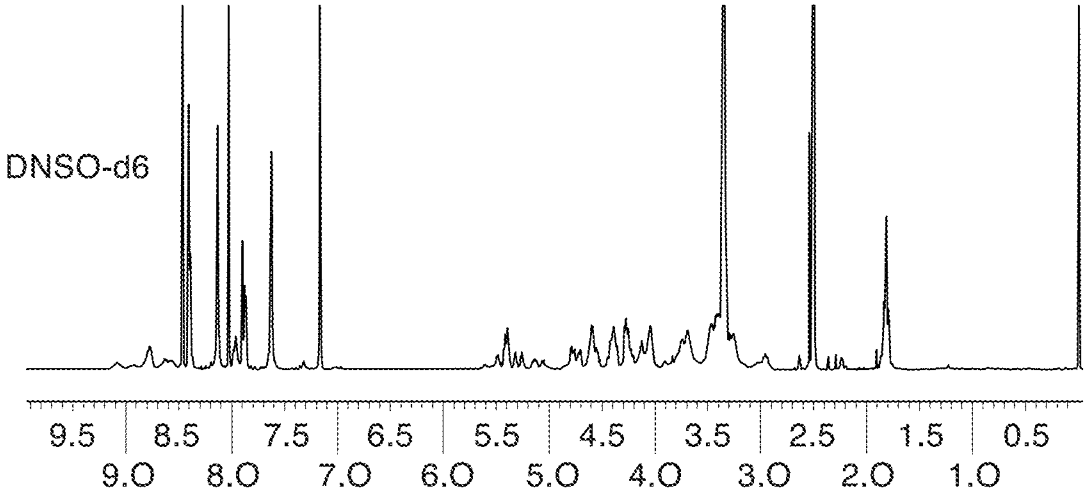
FIGS. 2A and 2B show proton NMR spectra of two iodinated compounds, in accordance with the present disclosure.
Figure 2B:
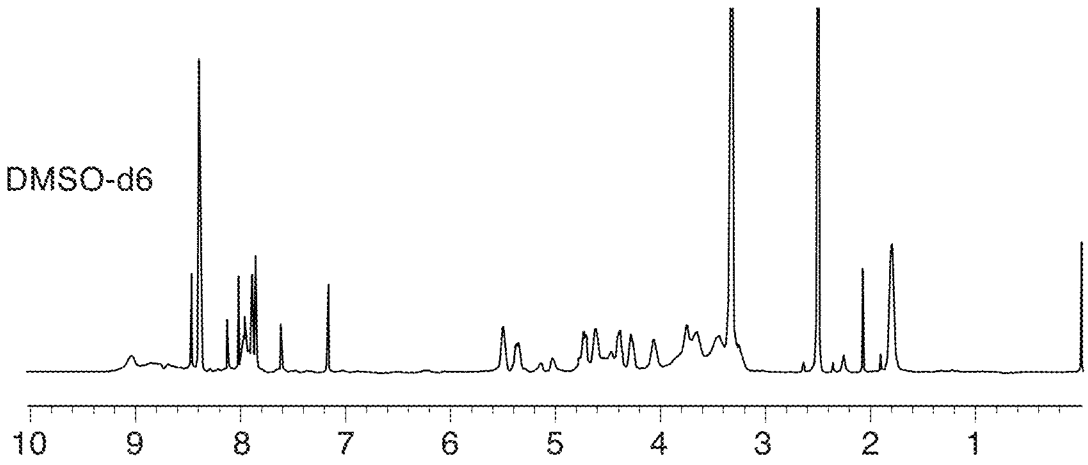

FIGS. 1A and 1B show the FTIR spectra of two of the Iohexol and Iodixanol derivatives, specifically, Iohexol derivative (I) and Iodixanol derivative (III). FIGS. 2A and 2B show proton NMR spectra of the two Iohexol and Iodixanol derivatives (in DMSO-d6 as solvent). The NMR spectra show some unreacted starting material residues, which should disappear upon further purification.

Example 2: Preparation of Iodinated PVA Polymer

To a dry 50 ml HEL Ltd PolyBLOCK® vessel (Borehamwood WD6 1GW, United Kingdom) degassed, purged with nitrogen and provided of a nitrogen blanket, dry DMSO (20 ml) was added stirring at 500 rpm. Then PVA (31-50 kDa, 99% hydrolysed); 5.0 g was added heating to 65° C. (internal probe) stirring at 500 rpm until all the solids was completely dissolved. After this time, 2,3,5-triiodobenzaldehyde 0.4 eq with respect to PVA-1,3-diol units (TIBA-prepared according to example 1 of WO2015/033092), followed by 2-sulfobenzaldehyde sodium salt, (FSAS, Sigma Aldrich UK) 0.075 eq.

After full dissolution, methanesulfonic acid (2.2 ml) was added dropwise stirring the reaction at 65° C. overnight. The orange solution was cooled to room temperature and poured dropwise in to 500 mL glass breaker containing acetone 200 mL. A white solid was recovered and re-dissolved in DMSO 50 mL and precipitated again in acetone 500 mL. The solid was collected on a Buchner funnel and the excess of acid neutralised with 0.1N NaOH solution (~100 mL) washing with deionised water until a neutral pH was achieved. The solid was then dried in a hi-vacuum oven at 28-32° C. overnight to give the desired product as off-white solid (3.0 g, ~70% w/w yield). A 20% (w/w) solution in DMSO was prepared.

Example 3: Preparation of Liquid Embolic Formulation

A liquid embolic formulation was prepared from iodinated PVA polymer (I-PVA) with hydrophilic functional groups and an iodinated compound in accordance with the present disclosure, dissolved in DMSO solvent. In particular, a solution containing I-PVA (18 wt %), Iodixanol derivative (III) from Example 1 (9.5 wt %) and DMSO (72.5% wt) was prepared by adding 3.6 g of I-PVA and 1.9 g of Iodixanol derivative (III) to a vial and gently mixing the powder together. 14.5 g of DMSO was then added to make a total 20 g solution. The vial was sealed and roller-mixed for at least 4 hours until both powders are fully solubilized in the solvent (DMSO). The vial was sterilized using dry-heat (121° C. for 0.5 hour).

Figure 3:
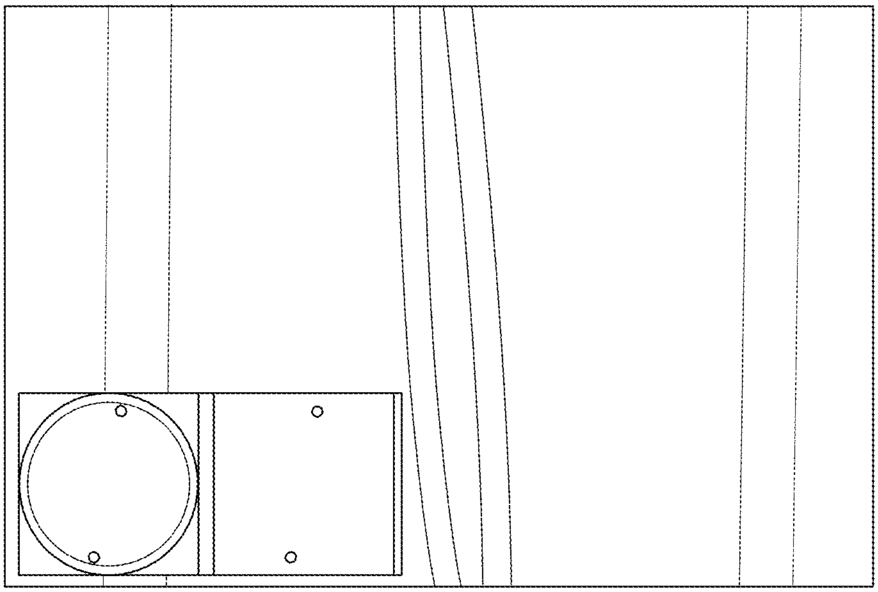
FIG. 3 shows micro-CT images of strands of a liquid embolic material in accordance with the present disclosure, within an agar phantom. The insets are micro-CT images of the dissection of the liquid embolic material.
Figure 4:
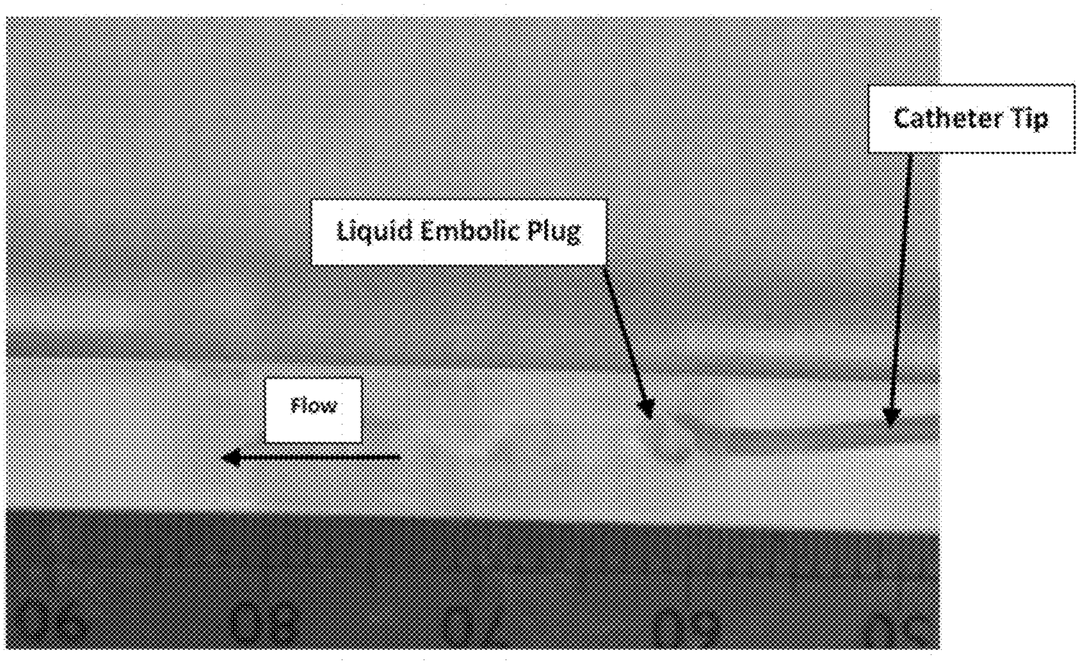
FIG. 4 is an optical image of an embolization created by delivery of a liquid embolic material in accordance with the present disclosure to a 5 mm silicone tube perfused a constant flow of phosphate buffered saline (PBS) at 400 ml/min of flow rate (at 37° C.).

Injectability was characterized by a dynamic viscosity (u) measurement using an Anton-Paar MCR 302 rheometer with a temperature sweep from 15° C. to 40° C. at 2.5° C./min, yielding a viscosity value at 20° C. of $\mu$=400 mPa s. Radiopacity (R) was characterized by micro-CT analysis to calculate the radiopacity in Hounsfield Unit (HU) of the liquid formulation, yielding a radiopacity value of R=7052 HU. Micro-CT images are presented in FIG. 3, which of shows strands of the liquid embolic material within an agar phantom. The insets of FIG. 3 are CT images of the dissection of the liquid embolic material. Embolization efficiency was shown by delivery of the liquid embolic material to a 5 mm silicone tube perfused to a constant flow of phosphate buffered saline (PBS) at 400 ml/min of flow rate (at 37° C.). Flow reduction greater than 99% was observed. FIG. 4 is an optical image of the resultant embolization.

Example 4: Radiopaque Coating on Balloon Catheter

Figure 5:
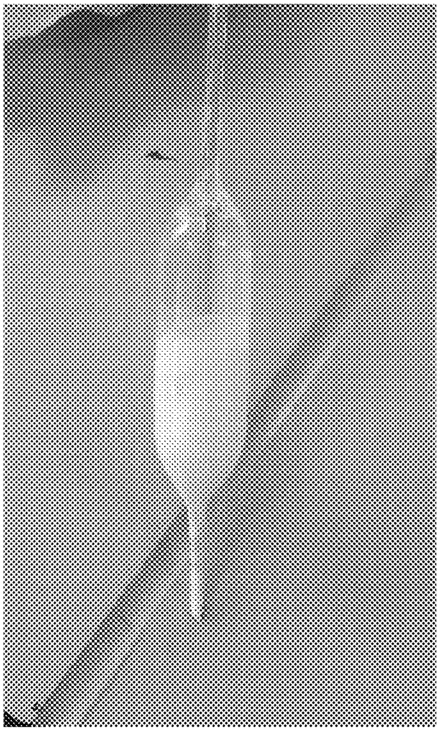
FIG. 5 is an optical image of a balloon that has been coated with a coating of PVA and an iodinated compound, in accordance with the present disclosure.
Figure 6:
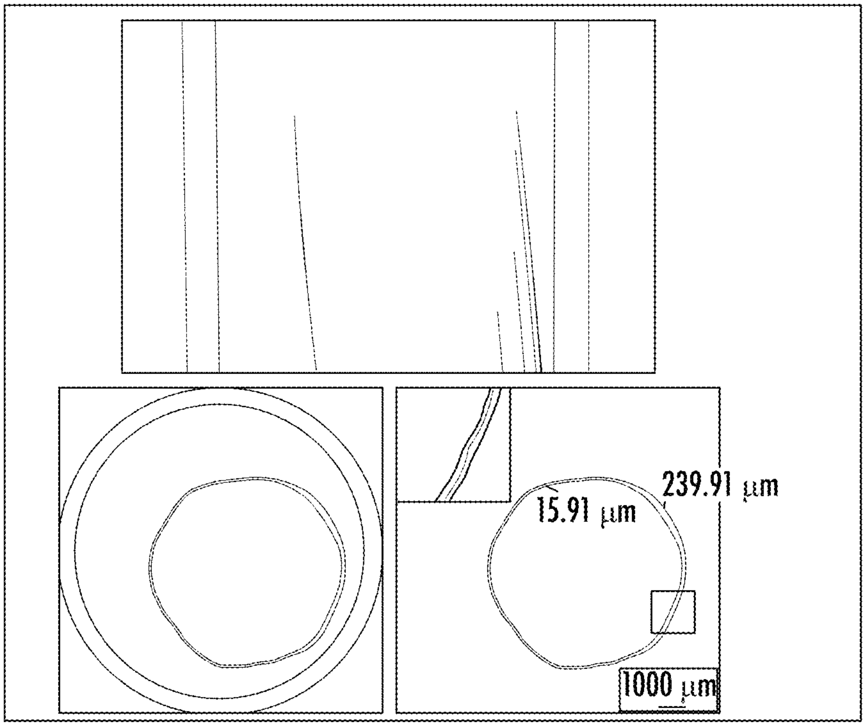
FIG. 6 is an illustration of μCT analysis of the coated balloon of FIG. 5 and a cross-sectional analysis of the same (insets).

PVA coating solutions were prepared in DMSO solvent at various concentrations with the radiopaque additive. In a specific case, PVA polymer (MW 31-50 kDa, 98% hydrolysed, available from Sigma-Aldrich) at 7% (w/w) was mixed with 8% to 23% (w/w) of iodixanol derivative in DMSO. A balloon catheter (Abbott Vascular Fox sv PTA Catheter (2-6 mm×120 mm), Abbott Laboratories, Chicago, IL, USA) was inflated and the balloon was dip coated in the aforementioned DMSO solution for 5 to 10 seconds, followed by placing the balloon into deionised water to allow exchange of water and DMSO. The resulting coating, shown in FIG. 5, was cohesive, flexible and was stable to repeated balloon inflation/deflation cycles. The coated balloon was analyzed by µCT, as shown in FIG. 6 (the lower images correspond to a cross-sectional analysis of the of the balloon). A radiopacity of 4700 Hounsfield Units (HU) was measured.

The invention claimed is:

1. A composition comprising one or more iodinated compounds that comprise at least one 2,4,6-triiodobenzene moiety in which more than one of the hydrogens at 1-, 3- and 5-positions of the at least one 2,4,6-triiodobenzene moiety is substituted by an iodinated substituent that comprises one or more iodophenyl-containing groups, wherein the one or more iodophenyl-containing groups are selected from iodophenyloxy groups, iodophenylcarbonyloxy groups, or iodophenyl groups coupled via a cyclic acetal group or a carbamate group.

2. The composition of claim 1, wherein the iodinated compounds comprise one or two 2,4,6-triiodobenzene moieties in which more than one of the hydrogens at 1-, 3- and 5-positions of each of the one or two 2,4,6-triiodobenzene moieties is substituted by the iodinated substituent that comprises one or more iodophenyl-containing groups.

3. The composition of claim 1, wherein the one or more iodophenyl-containing groups are selected from one or more of mono-iodophenyl-containing groups, di-iodophenyl containing groups, tri-iodophenyl-containing groups, tetra-iodophenyl-containing groups or penta-iodophenyl-containing groups.

4. The composition of claim 1, wherein the iodinated substituent comprises a $C_2$-$C_6$-alkyl-amino group in which $C_2$-$C_6$-alkyl hydrogens are substituted by (a) the one or more iodophenyl-containing groups and (b) zero, one or a plurality of hydroxyl groups.

5. The composition of claim 1, wherein the iodinated substituent is a $C_2$-$C_6$-alkyl-aminocarbonyl group or a $C_2$-$C_6$-alkyl-carbonylamino group in which $C_2$-$C_6$-alkyl hydrogens are substituted by (a) the one or more iodophenyl-containing groups and (b) zero, one or a plurality of hydroxyl groups.

6. The composition of claim 5, wherein the $C_2$-$C_6$-alkyl-aminocarbonyl group is a $C_3$-alkyl-aminocarbonyl group.

7. The composition of any of claim 1, wherein a molar ratio of hydroxyl groups to iodophenyl-containing groups ranges from 0:1 to 10:1.

8. A composition of claim 1, further comprising a polymer.

9. The composition of claim 8 having a radiopacity ranging from 10-1000 Hounsfield Units (HU).

10. The composition of claim 8 having an amount of iodine ranging from 5 to 40 wt % or an amount of iodine ranging from 50-900 mg $I/cm^3$.

11. A medical supply comprising (a) the composition of claim 1 and (b) a polymer.

12. The medical supply of claim 11, wherein the medical supply is an embolic composition.

13. The medical supply of claim 12, wherein the embolic composition is a liquid embolic composition.

14. The medical supply of claim 11, wherein the medical supply is a medical device.

15. The medical supply of claim 14, wherein the composition is in the form of a medical device coating.

* * * * *